United States Patent [19]
Dykstra et al.

[11] Patent Number: 5,935,982
[45] Date of Patent: *Aug. 10, 1999

[54] METHODS OF TREATING RETROVIRAL INFECTION AND COMPOUNDS USEFUL THEREFOR

[75] Inventors: Christine C. Dykstra, Auburn, Ala.; David Boykin, Atlanta, Ga.; Richard R. Tidwell, Pittsboro, N.C.

[73] Assignees: The University of North Carolina at Chapel Hill, Chapel Hill, N.C.; Auburn University, Auburn, Ala.; Georgia State Research Foundation, Inc., Atlanta, Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 08/808,321

[22] Filed: Feb. 28, 1997

[51] Int. Cl.$^6$ .................................................... A61K 31/415
[52] U.S. Cl. ............................................................ 514/394
[58] Field of Search .......................... 548/305.4; 514/394

[56] References Cited

U.S. PATENT DOCUMENTS

| | | | |
|---|---|---|---|
| 4,324,794 | 4/1982 | Tidwell et al. | 424/273 B |
| 5,585,091 | 12/1996 | Pelzer et al. | 424/60 |
| 5,602,172 | 2/1997 | Boykin et al. | 514/461 |
| 5,639,755 | 6/1997 | Dykstra et al. | 514/256 |
| 5,643,935 | 7/1997 | Dykstra et al. | 514/394 |
| 5,667,975 | 9/1997 | Dykstra et al. | 435/6 |
| 5,668,166 | 9/1997 | Tidwell et al. | 514/411 |
| 5,668,167 | 9/1997 | Tidwell et al. | 514/411 |

FOREIGN PATENT DOCUMENTS

| | | |
|---|---|---|
| 2839989 | 4/1980 | Germany . |
| 4212748 | 10/1993 | Germany . |
| WO94 08580 | 4/1994 | WIPO . |
| WO95 08540 | 3/1995 | WIPO . |
| WO95 19772 | 7/1995 | WIPO . |

OTHER PUBLICATIONS

Tidwell et al., Diarylamidine Derivatives with One or Both of the Aryl Moieties Consisting of an Indole or Indole–like Ring. Inhibitors of Arginine–Specific Esteroproteases, J. Med. Chem. vol. 21, No. 7, 613–623 (1978).

Tidwell et al., Suppression of respiratory syncytial virus infection in cotton rats by bis (5–amidino–2–benzimidazolyl) methane, Chemical Abstracts, vol. 101, No. 23, p. 24 (1984).

Tidwell et al., Suppression of Respiratory Syncytial Virus Infection in Cotton Rats by Bis (5–Amidino–2–Benzimidazolyl) Methane, Antimicrobial Agents and Chemotherapy, vol. 26, No. 4, 591–593 (1984).

Fairley et al., Structure, DNA Minor Groove Binding, and Base Pair Specificity of Alkyl–and Aryl–Linked Bis (amidinobenzimidazoles) and Bis(aminoindoles); J. Med. Chem. 1993, 36, 1746–1753 1993.

Dubovi et al., Inhibition of Respiratory Syncytial Virus–Host Cell Interactions by Mono–and Diamidines; (Antimicrobial Agents and Chemotherapy, vol. 19, No. 4, Apr. 1981, p. 649–656) 1981.

Sibertsev et al., Bioorg. Khim. (1995), 21(9), 731–736.

Tidwell et al., J. Med. Chem. (1978), 21(7), 613–623.

Primary Examiner—Mukund J. Shah
Assistant Examiner—Bruck Kifle
Attorney, Agent, or Firm—Myers Bigel Sibley & Sajovec

[57] ABSTRACT

The present invention provides methods for treating retroviral infection and methods of treating HIV infection. The methods of the present invention include administering compounds of the general Formula I:

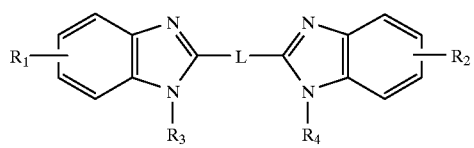

wherein L, $R_1$, $R_2$, $R_3$, $R_4$ are defined herein.

25 Claims, No Drawings

METHODS OF TREATING RETROVIRAL INFECTION AND COMPOUNDS USEFUL THEREFOR

FIELD OF THE INVENTION

The present invention relates to retroviruses, and more particularly to methods for the treatment of retroviral infections. The present invention also relates to compounds useful for the treatment of retroviral infections.

BACKGROUND OF THE INVENTION

The genome of the typical retrovirus encodes three primary enzymes that mediate the virus replication cycle. Reverse transcriptase converts the viral RNA genome into a double stranded DNA. Integrase nonspecifically inserts this DNA copy into the host cell genome, and protease cleaves viral structural and nonstructural proteins into their mature forms.

An essential step of the retroviral life cycle is the integration of its double-stranded DNA copy into the host genome. H. Sakai et al, *J. Virol.* 67:1169 (1993). This process requires highly conserved sequence recognition and cleaving steps. For this reason, a therapeutic agent that can interrupt this process should be an effective and specific antiviral agent. A protein at the C-terminus of the viral polymerase, integrase (IN), is the only viral protein required for this process. R. LaFemina et al.,*J. Virol.* 66:7414 (1992).

A. Fesen et al.,*Proc. Natl. Acad. Sci. USA* 90:2399 (1993) discuss investigations using an in vitro integrase assay of a variety of chemicals as potential human immunodeficiency virus type I (HIV-1) integrase inhibitors. The article reports several topoisomerase inhibitors, such as doxorubicin, mitoxantrose, ellipticines and quercetin as potent inhibitors. While some topoisomerase inhibitors were excellent anti-integrase agents, no correlation was observed with antiviral effects. This is believed to be at least partially due to the fact that a number of topoisomerase inhibitors have severe cytotoxic effects, depending upon their mechansim of inhibition.

R. LaFemina et al., *J. Virology* 56:7414 (1992) reports studies assessing the usefulness of the integrase enzyme as a target for specific HIV-1 anti-viral therapeutic agents by determining its absolute requirement for productive HIV-1 infection. The article reports the results of the introduction of specific amino acid substitution into recombinant integrase and assesses the ability of the mutant proteins to properly mediate specific and non-specific cleavage as well as integration.

SUMMARY OF THE INVENTION

As a first aspect, the present invention relates to methods for treating a retroviral infection in a subject in having a retroviral infection. The methods comprises administering to the subject, an effective amount of a dicationic bis-benzimidazole compound of Formula I:

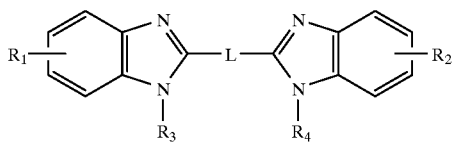

wherein:

L is a linking group selected from the group consisting of:

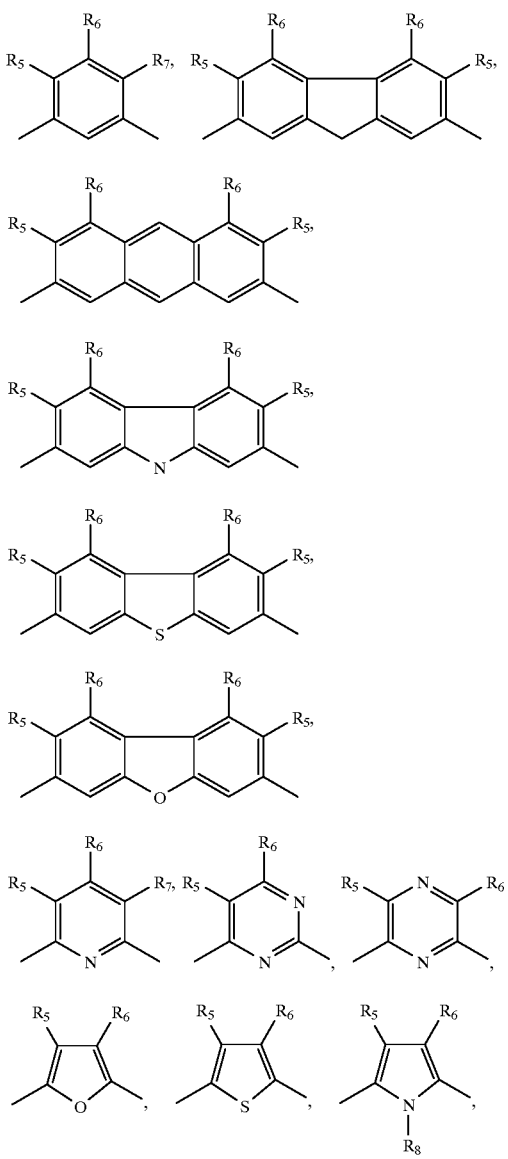

-continued

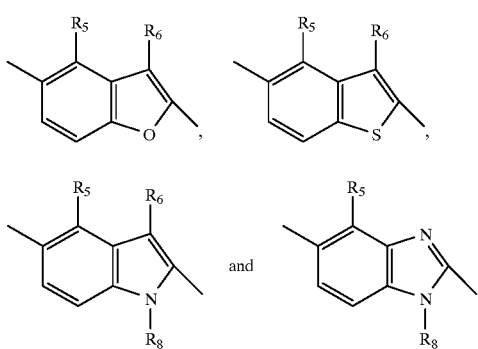

wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, or oxoarylalkyl;

$R_1$ and $R_2$ are each individually selected from the group consisting of

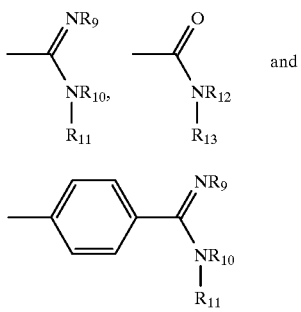

and wherein $R_9$ and $R_{10}$ are each individually selected from the group consisting of H, hydroxyl, and alkyl, or $R_9$ and $R_{10}$ together represent a group selected from the group consisting of —$(CH_2)_n$— where n is 2, 3, or 4 and

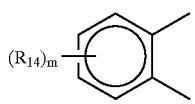

where m is 1, 2, or 3; and $R_{14}$ is H or —$CONHR_{15}R_{16}R_{17}$, wherein $R_{15}$ is lower alkyl and $R_{16}$ and $R_{17}$ are each independently selected from the group consisting of H and lower alkyl;

$R_{11}$ is H or alkyl;

$R_{12}$ is H, or alkyl;

$R_{13}$ is selected from the group consisting of alkyl, alkylamino, alkylmorpholino, and alkylaminophenyl; and $R_3$ and $R_4$ are each individually selected from the group consisting of H, alkyl and alkoxy. Pharmaceutically acceptable salts of the compounds of Formula I may also be employed. The effective amount of the compound of Formula I which is administered to the subject is an amount effective to treat the retroviral infection.

As a second aspect, the present invention relates to methods for treating an HIV infection in a subject in having an HIV infection. The methods comprises administering to the subject, an amount of a dicationic bis-benzimidazole compound of Formula I, or a pharmaceutically acceptable salt thereof, which is effective to treat the HIV infection.

As a third aspect, the present invention provides pharmaceutical formulations comprising compounds of Formula I, or pharmaceutically acceptable salts thereof, in an amount effective to carryout the methods of the present invention, together with a pharmaceutically acceptable carrier.

The foregoing and other aspects of the present invention are explained in detail in the detailed description and examples set forth below.

DETAILED DESCRIPTION OF THE INVENTION

As used herein, the term "alkyl" refers to $C_1$ through $C_8$ linear, branched, or cyclic alkyl. Specific examples of alkyl groups within the scope of the present invention include but are not limited to methyl, ethyl, propyl, isopropyl, cyclopropyl, n-butyl, isobutyl, tert-butyl, cyclobutyl, pentyl, isopenyl, cyclopentyl, hexyl, isohexyl, cyclohexyl, septyl, isoseptyl, octyl, and isooctyl, and the like. As used herein, the term "alkadienyl" refers to $C_2$ through $C_8$ unsaturated linear or branched alkyl. Specific examples of "alkadienyl" groups within the scope of the present invention include but are not limited to ethadienyl, 1-propadienyl, 2-propadienyl, 1-butadienyl, 2-butadienyl, 1,3-butadienyl, 1-hexadienyl, 1,3-hexadienyl, 2-hexadienyl, 2,4-hexadienyl, and the like. As used herein, the term "aryl" refers to 5 and 6-membered hydrocarbon and heterocyclic aromatic rings. Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like. The term "alkoxyl" as used herein refers to $C_1$ through $C_8$ linear, or branched alkoxy groups. Specific examples of alkoxyl groups within the scope of the present invention include but are not limited to methoxy, ethoxy, propoxy, isopropoxy, butoxy, isobutoxy, t-butoxy, pentoxy, hexoxy, octoxy, and the like.

Subjects which may be treated using the methods of the present invention include animal subjects, and typically include vertebrates. More specifically, subjects may include both mammalian (e.g., human, cat, dog, cow, horse, sheep, pig, monkey, ape, rat, mouse, rabbit, etc.) and avian subjects (e.g., chicken, turkey, duck, goose, quail, pheasant, etc.).

The methods of the present invention may be applied for the treatment of various retroviruses, i.e., the entire Retroviridae virus family. The family encompasses all viruses containing an RNA genome and an RNA-dependent DNA polymerase (reverse transcriptase) enzymatic activity. The family is divided into three subfamilies: (1) Oncovirinae, including all the oncogenic members and many closely related nononcogenic viruses; (2) Lentivirinae, the "slow" viruses, such as visna virus; and (3) Spumavirinae, the "foamy" viruses that induce persistent infections without any clinical disease. Retroviruses of interest include human retroviruses, such as human immunodeficiency virus type 1 (HIV-1), avian retroviruses, such as avian sarcoma and leukosis viruses of chickens (ASLVs), endogenous viruses of certain pheasant and quail species, reticuloendotheliosis virus of turkeys and related viruses of ducks and chickens, and lymphoproliferate disease virus of turkeys; feline C-type retroviruses, including feline leukemia virus (FeLV) and feline sarcoma virus (FeSV) and endogenous retroviruses (RD114 and CCC isolates); mink C-type retroviruses, including mink leukemia virus (MiLV); porcine C-type retroviruses; horse C-type retroviruses, including the equine infectious anemia virus (EIAV); bovine C-type retrovirus, including enzootic bovine leukosis or lymphosarcoma; sheep C-type retroviruses; and primate retroviruses, including prosimian C-type retroviruses, Simian sarcoma and gibbon ape leukemia C-type retroviruses, baboon C-type retroviruses, macaque C-type retroviruses, owl monkey C-type retroviruses, Colobus monkey C-type retroviruses, Mason-Pfizer monkey D-type retrovirus, Langur D-type retrovirus and squirrel monkey D-type retrovirus. See N. Teich, Taxonomy of Retroviruses in MOLECULAR BIOLOGY OF TUMOR VIRUSES, R. Weiss, et al. Eds., Cold Spring Harbor Laboratory, New York (2d ed. 1984), pps. 26–207.

The methods of the present invention include the administration of a compound of Formula I in an amount effective to treat the retrovirus. The compounds of Formula I include:

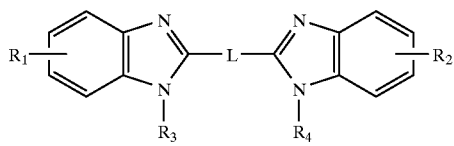

I wherein L is a linking group selected from the group consisting of:

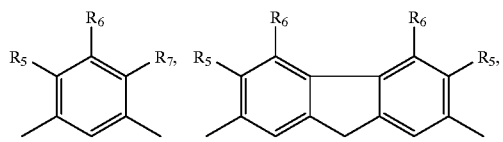

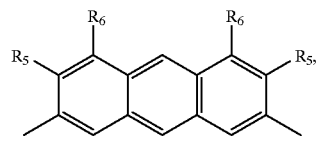

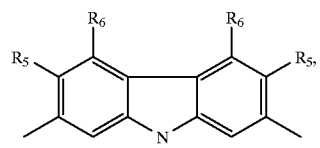

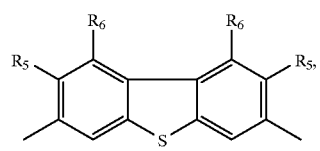

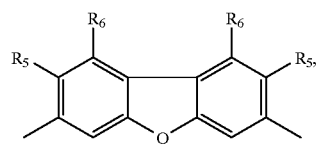

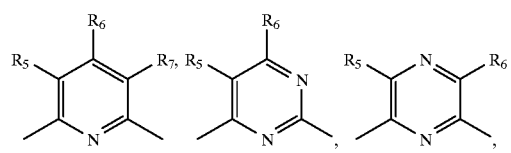

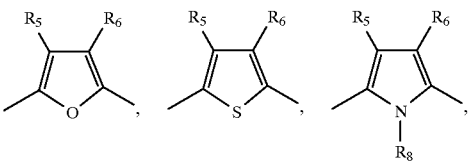

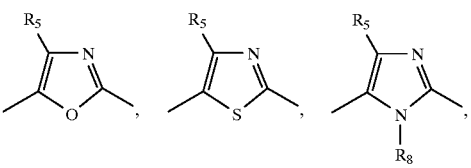

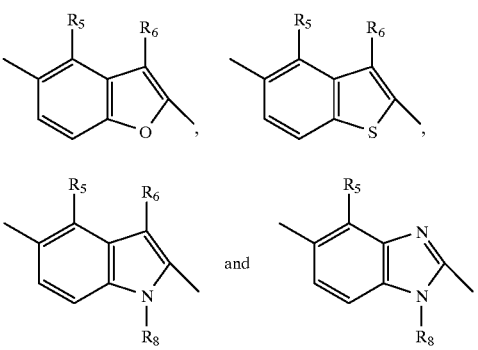

$R_5$, $R_6$, $R_7$, and $R_8$ are each individually selected from the group consisting of H, alkyl, halo, aryl, arylalkyl, aminoalkyl, aminoaryl, oxoalkyl, oxoaryl, or oxoarylalkyl; $R_1$ and $R_2$ are each individually selected from the group consisting of

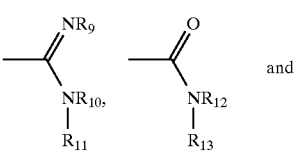

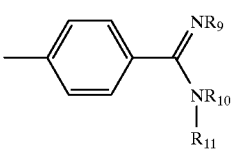

wherein $R_9$ and $R_{10}$ are each individually selected from the group consisting of H, hydroxyl, and alkyl, or $R_9$ and $R_{10}$ together represent a group selected from the group consisting of —(CH$_2$)$_n$— where n is 2, 3, or 4 and

where m is 1, 2, or 3; and $R_{14}$ is H or —CONHR$_{15}$R$_{16}$R$_{17}$, wherein $R_{15}$ is lower alkyl and $R_{16}$ and $R_{17}$ are each independently selected from the group consisting of H and lower alkyl; $R_{11}$ is H or alkyl; $R_{12}$ is H, or alkyl; $R_{13}$ is selected from the group consisting of alkyl, alkylamino, alkylmorpholino, and alkylaminophenyl; and $R_3$ and $R_4$ are each individually selected from the group consisting of H, alkyl and alkoxy.

Preferred compounds of Formula I include compounds wherein L is

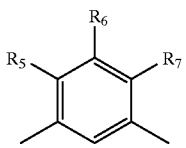

and $R_1$ and $R_2$ are each

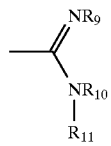

wherein $R_3$, $R_4$, $R_5$, $R_6$, $R_7$, $R_9$, $R_{10}$, and $R_{11}$, are defined as follows:

| $R_3$ | $R_4$ | $R_5$ | $R_6$ | $R_7$ | $R_9$ | $R_{10}$ | $R_{11}$ |
|---|---|---|---|---|---|---|---|
| H | H | H | H | H | H | H | H |
| H | H | H | H | H | —(CH$_2$)$_2$— | | H |
| H | H | H | H | H | —(CH$_2$)$_3$— | | H |
| H | H | H | H | H | H | H | isopropyl |
| H | H | H | H | H | H | H | isobutyl |
| H | H | H | H | H | H | H | cyclopentyl |
| H | H | H | H | H | H | H | cyclopropyl |

Another preferred compound of Formula I is the compound wherein L is

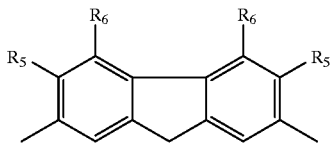

and $R_1$ and $R_2$ are each

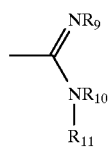

wherein $R_3$, $R_4$, $R_5$, $R_6$, $R_9$, and $R_{10}$ are each H, and $R_{11}$ is isopropyl.

Other preferred compounds of Formula I include those compounds
wherein L is

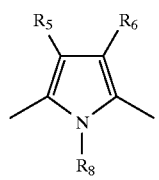

and $R_1$ and $R_2$ are each

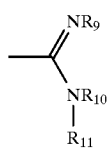

wherein $R_3$, $R_4$, $R_5$, $R_6$, $R_8$, $R_9$, $R_{10}$ and $R_{11}$ are defined as follows:

| $R_3$ | $R_4$ | $R_5$ | $R_6$ | $R_8$ | $R_9$ | $R_{10}$ | $R_{11}$ |
|---|---|---|---|---|---|---|---|
| H | H | H | H | H | H | H | H |
| H | H | H | H | CH$_3$ | H | H | H |
| H | H | H | H | H | —(CH$_2$)$_2$— | | H |
| H | H | H | H | CH$_3$ | —(CH$_2$)$_2$— | | H |
| H | H | H | H | H | H | H | isopropyl |
| H | H | H | H | CH$_3$ | H | H | isopropyl |
| H | H | H | H | H | H | H | cyclopentyl |
| H | H | H | H | CH$_3$ | H | H | cyclopentyl |

Still other preferred compounds of Formula I include compounds
wherein L is

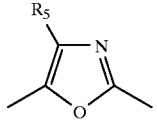

and $R_1$ and $R_2$ are each

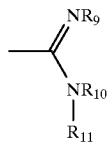

wherein $R_3$, $R_4$, $R_5$, $R_9$, $R_{10}$ and $R_{11}$ are defined as follows:

| $R_3$ | $R_4$ | $R_5$ | $R_9$ | $R_{10}$ | $R_{11}$ |
|---|---|---|---|---|---|
| H | H | H | H | H | H |
| H | H | H | —(CH$_2$)$_2$— | | H |
| H | H | H | H | H | isopropyl |
| H | H | H | H | H | cyclopentyl |

Another group of preferred compounds are include the compounds of Formula I wherein the L is

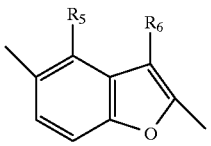

and $R_1$ and $R_2$ are each

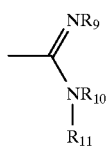

wherein $R_3$, $R_4$, $R_5$, $R_6$, $R_9$, $R_{10}$ and $R_{11}$ are defined as follows:

| $R_3$ | $R_4$ | $R_5$ | $R_6$ | $R_9$ | $R_{10}$ | $R_{11}$ |
|---|---|---|---|---|---|---|
| H | H | H | H | H | H | H |
| H | H | H | H | —(CH$_2$)$_2$— | | H |
| H | H | H | H | H | H | isopropyl |
| H | H | H | H | H | H | cyclopentyl |

Several of the compounds of Formula I are known in the art and may be synthesized in accordance with techniques previously described. According to one method, the compounds of Formula I can be prepared by condensation of an appropriate heterocyclic compound (i.e., pyrrole, pyridine, furan, etc.) dicarboxaldehyde (for example pyrrole-2,5-dicarboxaldehyde) which can be prepared according to the teaching of T. Cresp, et al., *J. Chem. Soc. Perkins Tran.* 1:2961 (1973) with the appropriate diaminophenyl compound (for example diaminobenzamidine prepared according to T. Fairley, et al., *Med. Chem.* 36:1746 (1993). The condensation reaction can be conducted according to the method of S. Kumar, et al., *Indian J. Chem.* 20B:254 (1981).

The diaminophenyl compounds can be prepared, for example, by reduction of nitro groups of 3,4-dinitrobromobenzene to form 3,4-diaminobromobenzene. Nitrilization of this compound to the corresponding 3,4-diaminonitrilebenzene can be conducted by reacting copper (I) cyanide with the thus prepared 3,4-dinitrobromobenzene in refluxing DMF according to the standard techniques. See, J. Spychala, et al., *European J. Med. Chem.* 29:363 (1994). The nitrile can then be converted to the imidate ester by the Pinner methodology, according to B. Das, et al., *J. Med. Chem.* 20:1219 (1977). The imidate ester can be converted into the compounds of Formula (I), for example, by reaction with ammonium or the appropriate aminoalkane or diaminoalkane (such as ethylenediamine, propylenediamine, etc.), to form an amidino group, an imidazolinyl group, an 1,4,5,6-tetrahydro-2-pyrimidinyl group, respectively. The bis-nitrile can also be converted to the bis-dicationic compound by fusion of the nitrile directly with the hydrochloride salt of the appropriate diamine by thermolysis. This technique is particularly useful for the preparation of compounds wherein the $R_1$ and $R_2$ groups together form a cyclic alkyl.

The compounds of Formula I above can also be prepared by first preparing an appropriate intermediate, such as 2,5-bis(5-bromo-2-benzimidazolyl)pyrrole by the base promoted condensation, for example, of 1-bromo-3,4-diaminobenzene and pyrrole-2,5-dicarboxaldehyde, according to the method of S. Kumar, et al., supra. The intermediate can then be obtained by nitrilization followed by imidate ester formation and conversion into the corresponding amidino as described above.

The compounds of Formula I having a fluorene linking group (L), i.e., compounds of the Formula:

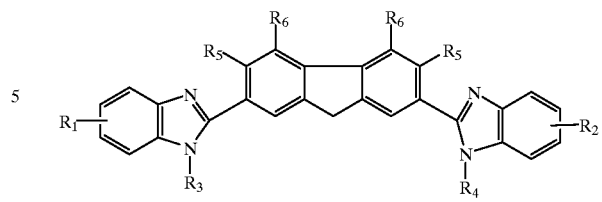

are new compounds which can be synthesized essentially in accordance with the following techniques.

Specific examples of the compounds of the present invention include but are not limited to:
2,5-bis(5-amidino-2-benzimidazolyl)pyrrole;
2,5-bis-[5-(2-imidazolinyl)-2-benzimidazolyl]pyrrole;
2,6-bis[5-(2-imidazolinyl)-2-benzimidazolyl]pyridine;
1-methyl-2,5-bis(5-amidino-2-benzimidazolyl)pyrrole;
1-methyl-2,5-bis[5-(2-imidazolyl)-2-benzimidazolyl] pyrrole;
1-methyl-2,5-bis[5-(1,4,5,6-tetrahydro-2-pyrimidinyl)-2-benzimidazolyl]pyrrole;
2,6-bis(5-amidino-2-benzimidazoyl)pyridine;
2,6-bis[5-(1,4,5,6-tetrahydro-2-pyrimidinyl)-2-benzimidazolyl]pyridine;
2,5-bis(5-amidino-2-benzimidazolyl)furan;
2,5-bis[5-(2-imidazolinyl)-2-benzimidazolyl]furan;
2,5-bis(5-N-isopropylamidino-2-benzimidazolyl)furan;
and physiologically acceptable salts thereof.

The compounds of the present invention may be provided and administered in the form or a free base, or may be in the form of a pharmaceutically acceptable salt thereof. Suitable pharmacuetically acceptable salts include inorganic acid addition salts such as hydrochloride, hydrobromide, sulfate, phosphate, and nitrate; organic acid addition salts such as acetate, propionate, succinate, lactate, glycolate, malate, tartrate, citrate, maleate, fumarate, methansulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt and N,N'-dibenzylethylenediamine salt; and salts with basic amino acid such as lysine salt and arginine salt.

The salt forms of the compounds of Formula I of the present invention may be prepared, in general, by reacting two equivalents of the free base of the compound of Formula I with the desired acid, in solution. After the reaction is complete, the salts are crystallized from solution by the addition of an appropriate amount of solvent in which the salt is insoluble.

As noted above, the present invention provides pharmaceutical formulations comprising the compounds of Formula I, or pharmaceutically acceptable salts thereof, in pharmaceutically acceptable carriers, preferably for aerosol, oral, and parenteral administration as discussed in greater detail below. Also, the present invention provides such compounds or salts thereof which have been lyophilized and which may be reconstituted to form pharmaceutically acceptable formulations for administration, as by intravenous or intramuscular injection.

The therapeutically effective dosage of any specific compound, the use of which is in the scope of the present invention, will vary somewhat from compound to compound, patient to patient, and will depend upon the condition of the patient and the route of delivery. As a general proposition, a dosage from about 0.1 to about 20 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where salt is employed. Typically a dosage from about 0.56 mg/kg to about 5 mg/kg will be employed. In certain circumstances, higher or lower doses may be also appropriate. The duration of the treatment may be once per day for a period of from two to three weeks and may continue for period of months or even years, for example, in treating chronic conditions. Lower doses given less frequently can be used to prevent or reduce the incidence of recurrence of the infection. The daily dose can be administered either by a single dose in the form of an individual dosage unit or several smaller dosage units or by multiple administration of subdivided dosages at certain intervals.

The present invention also provides pharmaceutical formulations, both for veterinary and for human medical use, which comprise the retroviral integrase inhibiting agent together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

The formulations include those suitable for oral, rectal, topical, nasal, ophthalmic or parenteral (including subcutaneous, intramuscular and intravenous) administration. Formulations suitable for aerosol, oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the integrase inhibiting agent as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tables comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient and pyrogen-free.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

In accordance with the preferred embodiments of the present method, a compound of Formula I, or a pharmaceutically acceptable salt thereof, may be administered orally or through inhalation as a solid, or may be administered intramuscularly or intravenously as a solution, suspension, or emulsion. Alternatively, the free base of the compound of Formula I, or a salt thereof may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

The present invention also provides pharmaceutical compositions suitable for intravenous or intramuscular injection. The pharmaceutical compositions comprise a compound of Formula I, or a pharmaceutically acceptable salt thereof, in any pharmaceutically acceptable carrier. If a solution is desired, water is the carrier of choice with respect to water-soluble compounds or salts, an organic vehicle, such as glycerol, propylene, glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filing should be done by an aseptic method. Sterilized closures may then be placed on the vials and, if desired, the vial contents may be lyophilized.

In addition to compounds of Formula I or their salts, the pharmaceutical compositions may contain other additives, such as pH adjusting additives. In particular, useful pH adjusting agents include acids, bases or buffers, such a sodium lactate, sodium acetate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula I, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into the subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Other pharmaceutical compositions may be prepared from the water-insoluble compounds of Formula I, or salts thereof, such as aqueous base emulsions. In such an instance, the composition will contain a sufficient amount of pharmaceutically acceptable emulsifying agent to emulsify the desired amount of the compound of Formula I or salt thereof. Particularly useful emulsifying agents include phosphatidyl cholines, and lecithin.

Further, the present invention provides liposomal formulations of the compounds of Formula I and salts thereof. The technology for forming liposomal suspensions is well known in the art. When the compound of Formula I or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula I or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired compound of Formula I or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds of salts. The liquid droplets or solid particles should have a particle size in the range of about 0.5 to about 5 microns. The solid particles can be obtained by processing the solid compound of Formula I, or a salt thereof, in any appropriate manner known in the art, such as by micronization. Most preferably, the size of the solid particles or droplets will be from about 1 to about 2 microns. In this respect, commercial nebulizers are available to achieve this purpose. Preferably, when the pharmaceutical formulation suitable for administration as an aerosol is in the form of a liquid, the formulation will comprise a water-soluble compound of Formula I or a salt thereof, in a carrier which comprises water. A surfactant may be present which lowers the surface tension of the formulation sufficiently to result in the formation of droplets within the desired size range when subjected to nebulization.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

The following examples are provided to illustrate the present invention, and should not be construed as limiting thereof. In these examples, "g" means grams, "mg" means milligrams, "μg" means micrograms, "mmol" means millimoles, "ml" means milliliter, "M" means molar, "mM" means millimolar, "UV" means ultraviolet, "HCl" means hydrogen chloride, "NaCl" means sodium chloride, "EDTA" means ethylenediaminetetraacetic acid, "MP" means melting point, and "°C." means degrees Celcius.

EXAMPLE 1

Preparation of 2,5-bis(5-amidino-2-benzimidazolyl) pyrrole 2,5-bis(5-amidino-2-benzimidazolyl)pyrrole. A solution of pyrrole-2,5-dicarboxaldehyde (Cresp, T., Sargent, M., *J. Chem. Soc. Perkin Trans.* 1:2961 (1973)) (0.25 g, 2 mmol), 3,4-diaminobenzamidine (Fairley T. A., Tidwell R. R., Donkor I., Naiman N. A., Ohemeng K. A., Bentley A. and Cory M. J., *Med. Chem.* 36:1746 (1993)) (0.6 g, 4 mmol) and 1,4-benzoquinone (0.432 g, 4 mmol) in ethanol (40 ml) was heated at reflux for 4 hours (under nitrogen) (Kumar, S., Konsal, V., Bhaduri, A., *Indian J. Chem.* 20B:254 (1981). The reaction mixture was cooled to room temperature and the dark solid was collected by filtration, washed with cold ethanol, anhydrous ether and dried to yield 0.45g (59%) of the free base. This solid was dissolved slowly in hot ethanol (300 ml) and filtered. The filtrate volume was reduced to 70 ml and acidified with HCl-saturated ethanol. After standing overnight in the refrigerator, the green solid was collected by filtration, washed with anhydrous ether and dried under vacuum to yield 0.5 g (76%) yield of solid. mp>300° C. $^1$HNMR (DMSO-$d_6$) (7.54 (s, 2H, pyrrole), 7.80 (dd, J=8.8 and 0.8 Hz, Ar—H, 2H), 7.87 (d, J=8.4 Hz, 2H, Ar—H), 8.25 (s, 2H, Ar—H), 9.18, 9.48 (brs, brs, NH). Anal. ($C_{20}N_{17}N_9$.3HCl.3$H_2O$) C,H,N. MS: m/e 384 (M+1).

EXAMPLE 2

Preparation of 2,5-bis-[5-(2-imidazolinyl)-2-benzimidazolyl]pyrrole 2,5-bis-[5-(2-imidazolinyl)-2-benzimidazolyl]pyrrole. A protocol similar to that used in Example 1 above was used for the condensation of pyrrole-2,5-dicarboxaldehyde and 2-(3,4-diaminophenyl)imidazoline to give a 86% yield of solid. mp>300° C. $^1$HNMR (DMSO-$d_6$) (4.04 (s, 8H, $NCH_2CH_2N$), 7.39 (s, 2H, pyrrole), 7.86 (d, J=8.8 Hz, 2H, Ar—H), 7.92 (dd, J=8.4 and 1.6 Hz, 2H, Ar—H), 8.44 (s, 2H, Ar—H), 10.71 (s, NH). Anal. ($C_{24}H_{21}N_9$.3HCl.4$H_2O$) C,H,N. MS: m/e 436 (M+1).

EXAMPLE 3

Preparation of 2,6-bis[5-(2-imidazolinyl)-2-benzimidazolyl]pyridine 2,6-bis[5-(2-imidazolinyl)-2-benzimidazolyl]pyridine. A protocol similar to that used in Examples 1 and 2 above was used for condensation of 2,6-pyridine carboxyaldehyde and 2-(3,4-diaminophenyl)imidazoline to give an 85% yield of solid. mp>300° C. $^1$HNMR (DMSO-d$_6$) (4.05 (s, 8H, N—CH$_2$CH$_2$N), 7.96 (m, 4H, Ar—H), 8.30 (t, 1H, pyridine), 8.49–8.51 (m, 4H, Ar—H), 10.71 (s, NH). Anal. (C$_{25}$H$_{21}$N$_9$.3HCl.3H$_2$O) C,H,N. MS: m/e 448 (M+1).

EXAMPLE 4

Preparation of 1-Methyl-2,5-bis(5-amidino-2-benzimidazolyl)pyrrole

1-Methyl-2,5-bis(5-amidino-2-benzimidazolyl)pyrrole. A protocol similar to that described above in Examples 1–3 was employed for the condensation of 3,4-diaminobenzarnidine (Fairley T. A., Tidwell R. R., Donkor I., Naiman N. A., Ohemeng K. A., Bentley A. and Cory M. J., *Med. Chem.* 36:1746 (1993)) with 1-methylpyrrole-2,-5-dicarboxaldehyde to yield 0.48g (46%) of product. mp>300° C.; $^1$HNMR (DMSO-d$_6$) (4.72 (s, 3H, CH$_3$—N), 7.33 (s, 2H, pyrrole), 7.73 (dd, J=8 and 1.2 Hz, 2H, Ar—H), 7.80 (d, J=8.4 Hz, Ar—H), 8.19 (s, 2H, Ar—H) 9.11, 9.38 (brs, brs, NH-amidine). Anal. (C$_{21}$H$_{19}$N$_9$.3HCl.H$_2$O) C,H,N. MS:m/e 398 (M+1).

EXAMPLE 5

Preparation of 1-methyl-2,5-bis[5-(2-imidazolyl)-2-benzimidazolyl]pyrrole 1-methyl-2,5-bis[5-(2-imidazolyl)-2-benzimidazolyl]pyrrole. A protocol similar to that described above in Examples 1–4 was employed for the condensation of 2-(3, 4-diaminophenyl)-imidazoline with 1-methylpyrrole-2,-5-dicarboxaldehyde. A yield of 83% of solid, mp>300° C., was obtained. $^1$HNMR (4.04 (s, 8H, NCH$_2$CH$_2$N), 4.72 (s, 3H, CH$_3$N), 7.30 (s, 2H, pyrrole), 7.84 (qAB, J=8.4 and 8 Hz, 4H, Ar—H), 8.36 (s, 2H, Ar—H), 10.60 (s, NH). Anal. (C$_{25}$H$_{23}$N$_9$.3HCl.3H$_2$O) C,H,N. MS: m/e 450 (M+1).

EXAMPLE 6

Preparation of 1-Methyl-2,5-bis[5-(1,4,5,6-tetrahydro-2-pyrimidinyl)-2-benzimidazolyl]pyrrole 1-Methyl-2,5-bis[5-(1,4,5,6-tetrahydro-2-pyrimidinyl)-2-benzimidazolyl]pyrrole. A protocol similar to that described above for Examples 1–5 was employed for the condensation of 2-(3,4-diaminophenyl)tetrahydropyrimidine with 1-methylpyrrole-2,5-dicarboxaldehyde. A yield of 83% of solid, mp>300° C., was obtained. $^1$HNMR (2.01 (m, 4H, CH$_2$), 3.52 (brs. 8H, CH$_2$N), 4.72 (s, 3H, CH$_3$N), 7.31 (s, 2H, pyrrole), 7.60 (d, J=8.4 Hz, 2H, Ar—H), 7.80 (d, J=8.4 Hz, 2H, AR—H), 8.06 (s, 2H, Ar—H), 9.99 (s, NH). Anal. (C$_{27}$H$_{27}$N$_9$.3HCl.4H$_2$O) C,H,N. MS: m/e 478 (M+1).

EXAMPLE 7

Preparation of 2,6-bis(5-amidino-2-benzimidazoyl) pyridine 2,6-bis(5-amidino-2-benzimidazolyl)pyridine. A protocol similar to that described in Examples 1–6 above was used to condense 2,6-pyridine dicarboxaldehyde with 3,4-diaminobenzamidine to yield 89% of a solid, mp>300° C. $^1$HNMR (DMSO-d$_6$) (7.79 (dd, J=8.4 and 1.6 Hz, 2H, Ar—H), 7.94 (d, J=8.4 Hz, 2H, Ar—H), 8.28–8.34 (m, 3H, Ar—H), pyridine), 8.51 (d, J=8Hz, 2H, pyridine), 9.12, 9.45 (brs, brs, NH). Anal. (C$_{21}$H$_{17}$N$_9$.3HCl.2H$_2$O) C,H,N. MS: m/e 396 (M+1).

EXAMPLE 8

Preparation of 2,6-bis[5-(1,4,5,6-tetrahydro-2-pyrimidinyl)-2-benzimidazolyl]pyridine 2,6-bis[5-(1,4,5,6-tetrahydro-2-pyrimidinyl)-2-benzimidazolyl]pyridine. A protocol similar to that described above in Examples 1–7 was used to condense 2,6-pyridine dicarboxyaldehyde with 2-(3,4-diaminophenyl) tetrahydropyrimidine to give an 89% yield of solid, mp>300° C. $^1$HNMR (DMSO-d$_6$) (2.03 (m, 4H, CH$_2$), 3.54 (brs, 8H, CH$_2$N), 7.66 (d, J=8.4 Hz, 2H, Ar—H), 7.84 (d, J=8.4 Hz, 2H, Ar—H), 8.17 (s, 2H, Ar—H), 8.29 (t, 1H, pyridine), 8.43 (d, J=8 Hz, 2H, pyridine), 10.04 (s, NH). Anal. (C$_{27}$H$_{25}$N$_9$.3HCl.4H$_2$O) C,H,N. MS: m/e 476 (M+1).

EXAMPLE 9

Preparation of 2,5-bis(5-amidino-2-benzimidazolyl) furan 2,5-bis(5-amidino-2-benzimidazolyl]furan. A protocol similar to that described above in Examples 1–8 above was used to condense 2,5-furan dicarboxyaldehyde with 3,4-diaminobenzamidine. A solution of 2,5-furan dicarboxyaldehyde (0.25 g, 2 mmol), 3,4-diaminobenzamidine (0.6 g, 4 mmol) and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether. The yellow-green solid was acidified with concentrated HCl. After standing overnight ether was added and the solid was collected by filtration, washed with dry ether, and dried in vacuum at 90° C. for 48 hours. Yield 0.5 g (52.2%) of the yellow-green powder, mp>300° C. MS (FAB): m/z 385 (M$^+$+1); HRMS: calc. mass (free base); 385.1525 (M$^+$+ 1); observed mass: 385.1535, $^1$H NMR (DMSO-d$_6$, TMS) δ: 9.30 s, 4H (N—H); 8.95 s, 4H (N—H); 8.19 s, 2H (phenyl); 7.81 d, 2H, J=8.8 Hz; 7.72 d, 2H, J=8.4 Hz; 7.60 s 2H (furan), $^{13}$C NMR (DMSO-d$_6$+D$_2$O) δ: 166.8; 146.3; 146.1; 142.2; 139.7; 123.4; 122.7; 117.1; 116.1; 115.4. Anal. (C$_{20}$H$_{16}$N$_8$O.2HCl.1.5H$_2$O) C,H,N.

EXAMPLE 10

Preparation of 2,5-bis[5-(2-imidazolinyl)-2-benzimidazolyl]furan 2,5-bis[5-(2-imidazolinyl)-2-benzimidazolyl]furan. A protocol similar to that described above in Examples 1–8 above was used to condense 2,5-furan dicarboxyaldehyde with 2-(3,4-diaminophenyl)imidazoline. A solution of 2,5-furan dicarboxyaldehyde (0.25 g, 2 mmol), 2-(3,4-diaminophenyl)imidazoline (0.7 g, 4 mmol) and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether. The yellow-green solid was acidified with concentrated HCl. After standing overnight ether was added and solid was collected by filtration, washed with dry ether, and dried in vacuum at 90° C. for 3 days. Yield 0.45 g (38.1%) of the green powder, mp>300° C. MS (FAB): m/z 437 (M$^+$+1); HRMS: calc. mass (free base): 437.1838 (M$^+$+1); observed mass: 437.1832, $^1$H NMR (DMSO-d$_6$, TMS) δ: 10.53 s, 4H (N—H); 8.38 s, 2H; 7.87 d, 2H, J=8.5 Hz; 7.83 d, 2H, J=8.2 Hz; 7.62 s, 2H; 4.04 s, 8H. $^{13}$C NMR (DMSO-d$_6$+D$_2$O, TMS): δ166.3; 146.2; 146.1; 142.3; 139.8; 123.7; 117.6; 116.9; 116.1; 115.5; 45.0. Anal. (C$_{24}$H$_{20}$N$_8$O.2HCl.5H$_2$O) C,H,N.

EXAMPLE 11

Preparation of 2,5-bis(5-N-isopropylamidino-2-benzimidazolyl)furan 2,5-bis(5-N-isopropylamidino-2-benzimidazolyl]furan. A protocol similar to that described above in Examples 1–8 above was used to condense 2,5-furan dicarboxyaldehyde with 3,4-diamino-N-isopropylbenzamidine. A solution of 2,5-furan dicarboxyaldehyde (0.25, 2 mmol), 3,4-diamino-N-isopropylbenzamidine (0.77 g, 4 mmol), and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether and dried. After drying the green solid was dissolved in anhydrous ethanol saturated with HCl (50 mL) and heated until boiling started, then allowed to cool. The green solid was collected by filtration, and dried in vacuum at 90° C. for 3 days. Yield 0.67 g (53.6%) of the yellow-green powder, mp>300° C. MS (FAB): m/z 469 (M$^+$+1); HRMS: calc. mass (free base): 469.2464 (M$^+$+1); observed mass: 469.2475, $^1$H NMR (DMSO-d$_6$, TMS): δ9.60+9.58 s+s, 2H (N—H); 9.45 s, 2H (N—H); 9.45 s 2H (N—H); 9.04 s, 2H (N—H); 8.06 s, 2H (phenyl); 7.82 d, 2H, J=8.4 Hz; 7.69 s, 2H (furan); 7.62 d, 2H, J=8.2 Hz; 4.09 m, 2H (CH), J=7.02 Hz; 1.32 d 12H (CH$_3$), J=6.3 Hz; $^{13}$C NMR (DMSO-d$_6$+D$_2$O, TMS):δ162.8; 145.9; 145.9; 140.9; 138.5; 124.5; 124.0; 116.9; 115.9; 115.9; 45.9; 21.7. Anal. (C$_{26}$H$_{28}$N$_8$O.3HCl.5H$_2$O) C,H,N.

EXAMPLE 12

Preparation of 2,5-Diformylbenzo[b]furan

Diisobutylaluminum halide (4.26 g, 0.03 mole; 30 mL of a 1M solution in cyclohexane) is added dropwise to a solution of 2,5-dicyanobenzo[b]furan (1.68g, 0.01 mole) in 150 mL dry methylenechloride at 15° C., under nitrogen. The mixture is stirred for 15 minutes and then allowed to reflux for 40 minutes. The reaction mixture is cooled and 100 mL 1M sulfuric acid is added slowly while keeping the temperature below 25° C. After addition of the sulfuric acid is complete the mixture is stirred for 1 hour and the dichloromethane layer is separated. The aqueous layer is extracted with 100 mL of dichloromethane and the two organic phases are combined and washed with 20% NaHCO3 (aqueous), dried over anhydrous sodium sulfate and the solvent is distilled to yield a residue. The residue is tritrated with 1:1 ether:hexane and an off-white solid forms which is filtered, dried in vacuum at 60° C. for 4 hours. The reaction yields 1.2 g of product (69% yield) having a meting point of 141–142° C. $^1$H NMR (DMSO-d$_6$/50° C.) 10.1 (s, 1H), 9.92 (s, 1H), 8.48 (d, 1H, J=0.8), 8.10 (s, 1H), 8.08 (dd, 1H, J=8, J=8.8), 7.90 (d, 1H, J=8.8). $^{13}$C NMR (DMSO-d$_6$/50° C.) 191.8, 180.6, 158.1, 153.6, 132.9, 128.9, 127.5, 126.9, 118.8, 113.1.

Analysis calculated for C$_{10}$H$_6$O$_3$.0.2H$_2$O (177.75) C:67.56; H:3.67; found C:67.83; H:3.59.

EXAMPLE 13

Preparation of 2,5-Bis[2-(5N-substituted amidino)benzimidazoyl]benzo[b]furan

A mixture of 2,5-diformylbenzo[b]furan (0.174 g, 0.001 mole) 1,4-benzoquinone (0.216 g, 0.002 mole) and 4-substituted amidino-1,2-diaminobenzene (0.002 mole) in 30 mL dry ethanol is heated at reflux in an inert atmosphere for 8 hours. The volume is reduced to half under vacuum and diluted with dry ether and a colored solid forms. The solid is filtered and washed with dry ether. Then the solid is suspended in 10 mL absolute methanol and treated with 10 mL saturated methanolic HCl, and the mixture is stirred at 40° C. for 30 minutes. The solvent is distilled under vacuum, tritrated with dry ether and then filtered, washed with ether and dried in vacuum at 70° C. for 12 hours to yield 69–77% product.

EXAMPLE 14

Preparation of 2,5-Bis[2-(5-guanylbenzimidazoylinyl)benzo[b]furan tetrahydrochloride A bluish gray solid is obtained in 76% yield using the method of Example 13. The solid has a melting point of 332–334° C. $^1$H NMR (DMSO-d$_6$/D$_2$O/80° C.) 8.6 (s, 1H), 8.27 (d, 1H, J=8), 8.19 (d, 2H, J=9.6), 7.89 (d, 1H, J=8.8), 7.87 (s, 1H), 7.83 (d, 1H, J=8.4), 7.78 (d, 1H, J=8.4), 7.73 (d, 1H, J=8.4), 7.68 (d, 1H, J=8). $^{13}$C NMR (DMSO-d$_6$/D$_2$O/80° C.) 166.4, 165.9, 153.5, 147.4, 145.4, 141.6, 139.9, 139.1, 136.9, 128.6, 126.2, 123.3, 122.9, 122.6, 122.2, 122.1, 116.9, 115.8, 115.5, 115.0, 112.8, 108.6.

Analysis calculated for C$_{24}$H$_{18}$N$_8$O.3HCl.H$_2$O (561.86) C:51.30; H:4.12; N:19.94; found C:51.72; H:4.14; N:19.64.

EXAMPLE 15

Preparation of 2,5-Bis{2-[5-(N-isopropylamidino)benzimidazolinyl]}benzo[b]furan tetrahydrochloride A metallic greenish solid is obtained in 69% yield having a melting point of 285–290° C. using the method of Example 13. $^1$H NMR (DMSO-d$_6$/80° C.) 8.71 (s, 1H), 8.36 (d, 1H, J=8.8), 8.08 (d, 2H, J=9.2), 7.98 (d, 1H, J=8.8), 7.96 (s, 1H), 7.85 (d, 1H, J=8.8), 7.82 (d, 1H, J=8.8), 7.64 (d, 1H, J=8.8), 7.61 (d, 1H, J=8.8), 4.02 (q, 2H, J=6), 1.32 (d, 12H, J=6). $^{13}$C NMR (DMSO-d$_6$/D$_2$O/80° C.) 162.9, 162.6, 157.5, 152.9, 147.4, 145.3, 141.1, 138.7, 137.8, 134.9, 129.2, 126.9, 125.7, 125.0, 124.5, 123.8, 123.2, 121.4, 116.9, 116.1, 115.7, 115.5, 113.9, 109.4, 46.2, 46.1, 21.6.

Analysis calculated for C$_{30}$H$_{30}$N$_8$O.4HCl.0.5H$_2$O (673.47) C:53.49; H:5.23; N:16.64; found C:53.53; H:5.29; N:16.45.

EXAMPLE 16

Preparation of 2,5-Bis-{2-[5-(N-cyclopentylamidino)benzimidazoyl]}benzo[b]furan tetrahydrochloride A grey solid is obtained in 73% yield having a melting point of 290–294° C. using the method of Example 13. $^1$H NMR (DMSO-d$_6$/D$_2$O/80° C.) 8.62 (s, 1H), 8.27 (d, 1H, J=8.8), 8.08 (s, 1H), 8.05 (s, 1H), 7.95 (d, 1H, J=8.8), 7.90 (s, 1H), 7.84 (d, 1H, J=8.8), 7.79 (d, 1H, J=8.4), 7.64 (d, 1H, J=8.4), 7.57 (d, 1H, J=8.8), 4.14 (br, 2H), 2.13 (2.06 (m, 4H), 1.81–1.56 (m, 12H). $^{13}$C NMR (DMSO-d$_6$/D$_2$O/80° C.) 163.4, 163.1, 156.9, 153.2, 147.6, 145.2, 141.1, 138.8, 136.2, 128.9, 126.5, 124.5, 124.1, 123.9, 123.5, 122.5, 122.4, 116.9, 116.1, 115.8, 115.7, 115.1, 113.2, 108.8, 54.9, 54.8, 31.7, 23.9.

Analysis calculated for C$_{34}$H$_{34}$N$_8$O.4HCl (716.53) C:56.99; H:5.34; N:15.64; found C:56.89; H:5.34; N:15.53.

EXAMPLE 17

Preparation of 2,7-Diformylfluorene

To a stirred solution of 2,7-dicyanofluorene (2.16 g, 0.01 mole) in 150 mL dry methylene chloride, is added diisobutylaluminum hydride (1M in cyclohexane, 4.26 g, 0.003 mole) under nitrogen at room temperature. The suspension is heated at 40° C. for 1 hour, cooled, and 100 mL of 1M sulfric acid is added dropwise and stirred for 1 hour. A yellow solid precipitates and is filtered to yield 1.6 g (72%) of product having a melting point of 218–220° C. $^1$H NMR (DMSO-d$_6$/90° C.) 10.08 (s, 2H), 8.16 (d, 2H, J=8.0), 8.11 (s, 2H), 7.95 (d, 2H, J=8.0), 4.10 (s, 2H). $^{13}$C NMR (DMSO-d$_6$/90° C.) 191.9, 145.0, 144.7, 135.6, 128.5, 125.4, 121.1, 36.0. MS m/w 222 (M$^+$).

EXAMPLE 18

Preparation of 2,7-Bis{2-[5-(N-isopropylamidino) benzimidazolinyl]}fluorene tetrahydrochloride A mixture fo 2,7-diformylfluorene (0.222 g, 0.001 mole), 1.4-benzoquinone (0.216 g, 0.002 mole), and 4-(N-isopropylamidino)-1,2-phenylene diamine (0.457 g, 0.002 mole) in 50 mL of dry ethanol is heated at reflux for 8 hours under nitrogen. The volume is reduced to 15–18 mL and the product is filtered, washed with ether:ethanol (2:1), and the solid is dried. The solid is then suspended in 20 mL absolute methanol and saturated with dry HCl gas, stirred at 40° C. for 2 hours. The volume of the solid is reduced under vacuum, the residue is tritrated with dry ether and the dark purple green solid is filtered and dried under vacuum at 70° C. for 2 hours. The reaction yields 0.51 g (72%) of product having a melting point of 310–313° C. $^1$H NMR (DMSO-d$_6$/D$_2$O/90° C.) 8.53 (s, 2H), 8.34 (d, 2H, J=8.4), 8.22 (d, 2H, J=8.4), 8.11 (s, 2H), 7.85 (d, 2H, J=8.4), 7.65 (d, 2H, J=8.4), 4.23 (s, 2H), 4.09 (quintet, 2H, J=6.4), 1.33 (d, 12H, J=6.4). $^{13}$C NMR (DMSO-d$_6$/D$_2$O/90° C.) 162.22, 153.1, 144.9, 143.5, 138.7, 136.3, 126.9, 125.7, 124.3, 123.6, 121.7, 115.6, 114.7, 45.3, 36.7, 21.1.

Analysis calculated for $C_{35}H_{34}N_8 \cdot 4HCl$ (712.55) C:58.99; H:5.37; N:15.73; found C:59.14; H:5.59; N:15.43.

EXAMPLE 19

Structures of Select Compounds

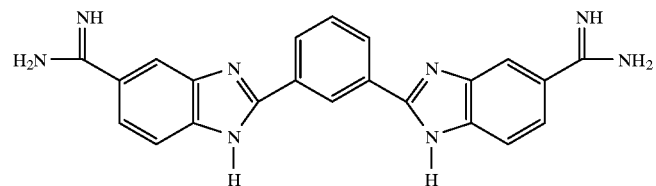

S-1

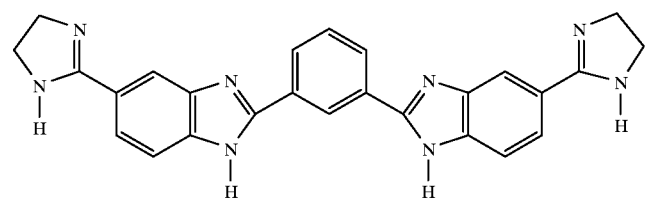

S-2

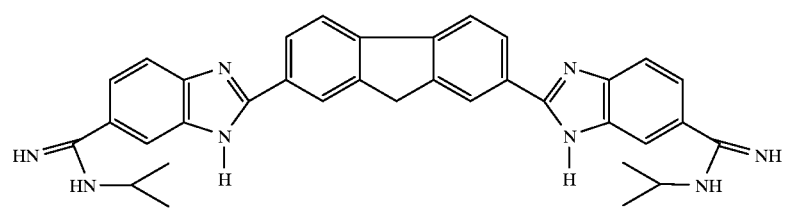

S-3

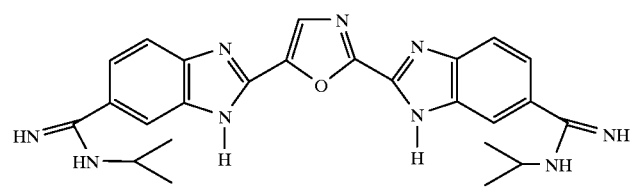

S-4

S-5
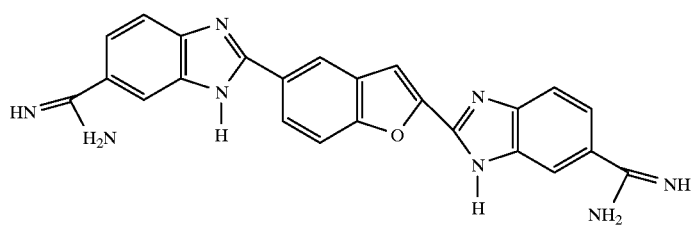
S-6
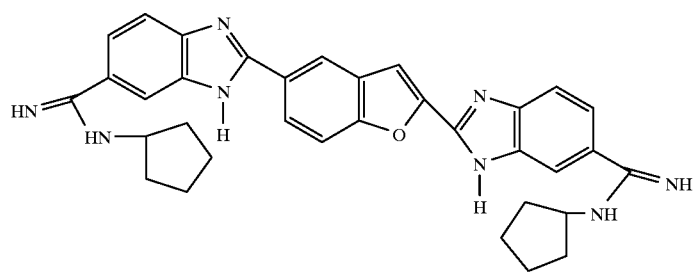
S-7
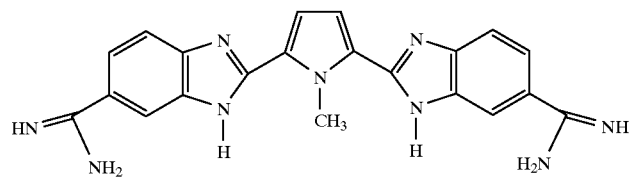
S-8
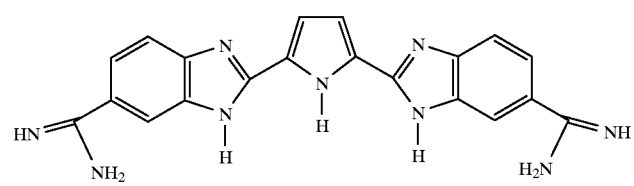
S-9
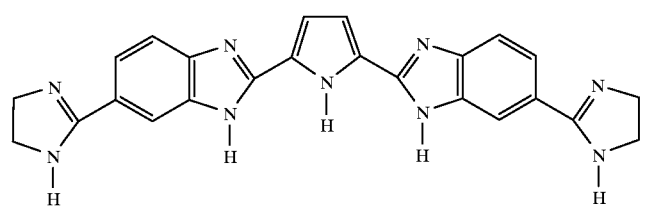
S-10
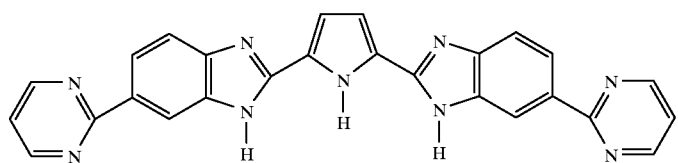
S-11
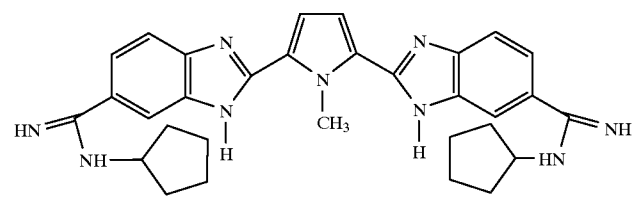

-continued

S-12
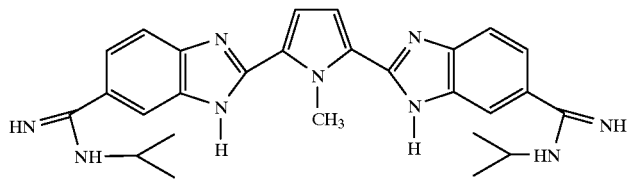

S-13
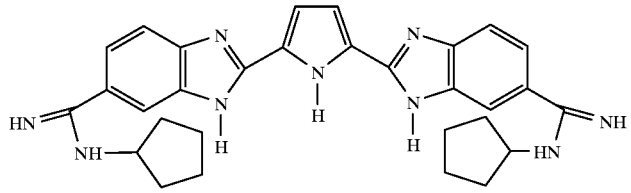

S-14
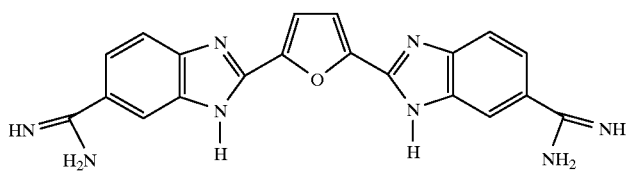

S-15
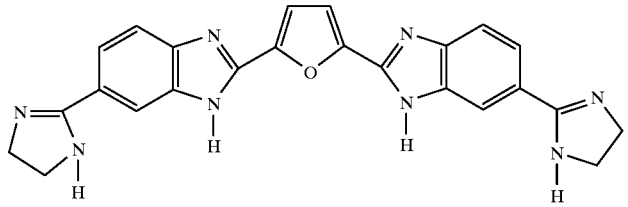

S-16
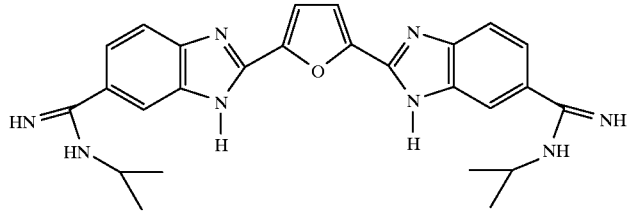

EXAMPLE 20

Preparation and Assay of Integrase Protein

Purification of Integrase Protein. Integrase was overproduced in E. coli from an inducible plasmid containing the integrase sequence under control of a lacI-regulated T7 polymerase using the integrase coding domain from the HXB2 clone of HIV-1 DNA (L. Ratner et al, AIDS Res. Hum. Retroviruses 3:57 (1987)), pT7fl1-IN. A one liter culture at an O.D. of 0.6 was induced by the addition of IPTG to 0.5 mM. After three hours, the cells were harvested by centrifugation and the pellets were stored at −70° C.

The integrase protein was purified by a modification of the method of Sherman and Fyfe, Proc. Natl. Acad. Sci. USA 87:5119 (1990). The cells were lysed by thawing in a buffer (50 mM Tris-HCl pH 7.5, 5 mM dithiothreitol, 1 mM EDTA, 1 mg/ml lysozyme) on ice at 6 ml/g bacterial pellet for 30 minutes, and then incubating at 37° C. for 5 minutes. The lysate was centrifuged at 12,000×g for one hour. The pellets were resuspended in 50 mM Tris-HCl, pH 7.5, 1 mM dithiothreitol, 1 mM EDTA, 1M NaCl (4 ml/g original bacteria). The homogenate was stirred for 30 minutes at 4° C. and recentrifuged for 30 minutes at 12,000×g.

The supernatant was made 0.8M in ammonium sulfate by the slow addition of powder with stirring over a 30 minute period. The extract was then centrifuged to remove any precipitate and applied to a phenyl sepharose column. After a 50 ml wash with high salt buffer (50 mM Tris-HCl, 1 mM EDTA, 5 mM DTT, 2M NaCl), the protein was eluted with a gradient from high salt to O salt buffer containing 10% (weight/vol) glycerol and further purified through a G75 Sephadex column to remove background nuclease. A one liter culture generates enough integrase activity to perform over a thousand drug inhibition assays.

Assays of Integrase Activity. The enzyme purification steps were monitored by an endonuclease/nicking assay and western blots utilizing a monoclonal antibody to integrase generated by W. Osheroff and R. Swanstrom at UNC—Chapel Hill. Supercoiled pBluescriptKS+II (0.3 μg) was incubated with column fractions in a buffer containing 20 mM Tris-HCl, pH 8.0, 5 mM 2-mercaptoethanol, and 2 mM $MnCl_2$ for 30 minutes at 37° C. The reactions were stopped by the addition of SDS to 1% and cleavage of the DNA substrate is assessed by electrophoresis through a 0.8% agarose gel stained with ethidium bromide and photographed under UV illumination.

Cleavage of specific sites is assessed as described in Sherman et al., supra, except that the assay buffer was the same as that reported by Chow et al, *Science* 255:723 (1992). The substrate employed is the same as that described for use in the dumbell assay described in Chow et al., *J. Virol.* 68:7869 (1994), the disclosure of which is incorporated herein by reference in its entirety. Essentially, the assay is performed with an oligonucleotide of 31 nucleotides that is self-annealing to form a dumbell shape with a nick therein. This substrate mimics the integrated virus and is specifically recognized by integrase to release 2 fragments. When the substrate is end-labeled with $\gamma^{32}P$-ATP and T4 polynucleotide kinase, and treated with integrase protein, the product is site-specific cleavage of the substrate to form a very different molecular weight when electrophoresed on a denaturing polyacrylamide gel. This allows the reaction to be more easily quantitated with the phosphorimager. This assay represents the step of the integrase reaction where integrase completes its action. The $IC_{50}$ value reported in Table 1 is generated by regression analysis of the percent control reaction with integrase at various drug concentrations. Initial screening of the compounds was performed at a constant 10 μM concentration for each test compound. Those with activity at 10 μM, were then used to identify $IC_{50}$ values.

The other assay used consisted of the single 20 mer oligonucleotides corresponding to either the U5 or U3 ends of HIV-1 are end-labeled with $^{32}P$, annealed with its complement, purified, and used under the same conditions as described above for the endonuclease assay. Reaction products are denatured with formamide, electrophoresed through 20% denaturing polyacrylamide gels and visualized by autoradiography. Both cleavage and ligation activity can be assessed from one gel. To assess the ligation activity alone, "precleaved" substrate that had the -2 cleavage artificially produced by using a radiolabelled 18 mer oligonucleotide was also used for some experiments Results are reported in Table 2 below.

EXAMPLE 21

Virus and Cell Cultures

Cell lines used were CEM cells, a human T-cell lymphona cell line, A. Kaplan et al, *J. Virol.* 67:4050–5 (1993), and Magic cells, J. Kimpton et al, *J. Virol.* 66:2232 (1992). The CEM cells were grown in RPMI-1640 medium supplemented with 5% FCS. The Magic Cells, a HELA derivative, were grown in DMEM/H supplemented with 5% FCS, G418 (20 mg/ml) and Hygromycin (10 mg/ml). The HIV isolate was strain HXB2, originally from Lee Ratner in the laboratory of Robert Gallo at the National Institutes of Health.

Results are reported in Table 2 below.

EXAMPLE 22

Toxicity Assays

Three different toxicity tests were performed on the cell lines used to measure virus infectivity.

The initial test for toxicity utilized the XTT Assay as described by Weislow et al, *J. Natl. Cancer Inst.* 81:577 (1989). This is the standard assay used originally to measure cell toxicity by potential reverse transcriptase inhibitors. Briefly, cells were grown to cells/ml and drug dilutions were added to the medium. After two days incubation, XTT reagent is added and incubation is continued for 4 hours at 37° C. Following incubation, the plates are read at 450 minus 650 nm (the 650 value is the backround value which is automatically subtracted) with controls of media+XTT reagent without cells, and cells+media without reagent. Also a control of cells+media+XTT reagent was run for each plate. Medium without phenol red was employed to minimize background color as the XTT reagent goes from colorless (unreduced) to orange (reduced). The XTT reagent was freshly prepared on the day of assay as follows: 1 mg/ml of XTT in 0.01M phenazine methosulfate. The phenazine methosulfate solution was prepared ahead of time and stored at 4° C. in a dark bottle. The XTT reagent is added to the microtiter wells at 24 ul per 100 ul of medium. The O.D. was measured on a Vmax plate reader from Molecular Devices Co. with data reduction. Results are expressed as percent of untreated controls. The least toxic compounds were Compounds A, B, and F with toxicities values at 500 μM or greater.

Next, a plating efficiency test measured the ability of the cell to grow after incubation with drug for a number of days. Magic cells were grown from an initial cell concentration of 0.8×104 with or without various concentrations of test compound for 6 days. Plating ability of the cells was assessed by plating dilutions of each culture on plastic. Colony forming units were determined after growth for two to four days by counting colonies after staining the plates. Each sample was plated in duplicate and the colony number averaged.

The third test for cell toxicity assessed growth rate in the presence of the test compound versus a control culture. Magic cells were grown over a period of 15 days with or without various dilutions of test compound. Aliquots were removed every other day and the cells were counted in a hemocytometer.

Results are reported in Table 2 below.

EXAMPLE 23

Integrase Inhibition Assays

Testing as Integrase Inhibitors. Integrase overproduced in *E. coli* was purified as described above in accordance with Sherman et al, supra, and used in drug inhibition assays. The integrase preparation used for these studies was extremely pure and did not contain any contaminating nuclease activity. Dilutions of the inhibitor compounds described in Example 1 above were mixed with substrate before the addition of enzyme. The Assay was the same as described in Example 20 and used the substrate described in Example 20. Each assay was performed in duplicate. Radioactivity in bands on dried gels were quantitated with a Phosphor imager to assess drug effects on both the cleavage, nuclease, and ligation products. The $IC_{50}$ values for integrase inhibition were calculated for both the cleaving and joining parts of the integrase reaction after determining the % inhibition of the control reaction for a series of drug concentrations. These results are shown in Table 2 below.

TABLE 2

Summary of Assay Results

| Compound | Toxicity TD$_{50}$($\mu$M) | Anti-HIV IC$_{50}$($\mu$M) | Index TD$_{50}$/IC$_{50}$ | Integrase IC$_{50}$($\mu$M) |
|---|---|---|---|---|
| S-1 | 40.02 | | | 1.0 |
| S-2 | | | | >10 |
| S-3 | | | | <10 |
| S-4 | | | | <10 |
| S-5 | | 19.75 | | <10 |
| S-6 | | 30.05 | | 1.4 |
| S-7 | 90.30 | 63.30 | 1.42 | 0.85 |
| S-8 | | | | 0.5 |
| S-9 | 212.59 | | | >10 |
| S-10 | | | | <10 |
| S-11 | 732.02 | | | >10 |
| S-12 | 288.82 | | | <10 |
| S-13 | 78.21 | | | <5 |
| S-14 | 81.49 | 26.71 | 3.05 | 0.9 |
| S-15 | 41.92 | 8.01 | 5.23 | 0.6 |
| S-16 | 237.52 | 1.39 | 170.88 | <10 |

Although not wishing to be bound by any theory or explanation of the invention, these compounds are currently believed to bind in the double stranded DNA minor groove with an AT bias (see T. Fairley et al, *J. Med. Chem.* 36:1746 (1993)), and most likely inhibit integrase by preventing the binding of integrase to its recognition sequences at the long terminal repeat ("LTR") of the virus. This proposed mechanism is supported by the observation that both cleavage and integration are equally effected by the compounds. Either DNA sequence specificity and/or direct interactions with the integrase protein are also currently believed to be possibly involved in the compound mechanism. Since integrase functions as a multimer, K. S. Jones et al, *J. Biol. Chem.* 267:16037 (1992), it is also possible that the DNA binding of the compounds somehow effects the multimer equilibrium.

The results indicate that DNA binding strength alone, however, is not the determining factor. Either DNA sequence specificity and/or direct interactions with the integrase protein are currently also believed to be possibly involved. Since nucleosomes have been shown to be precisely positioned in the 5' LTR of HIV-1, A. Fesen et al., *Proc. Natl. Acad. Sci. USA* 90:2399 (1993), such phasing could be one other way that the dicationic, groove binding drugs interfere with integrase action.

EXAMPLE 24

HIV-1 Inhibition Assays

The magi cell assay described by Kimpton et al., supra, was used as described. This assay identifies individual cells infected with HIV-1 by the expression of tat, which transactivates an endogenous copy of the HIV-1 LTR linked to the lac2 reporter gene after integration, inducing $\beta$-galactosidase expression when Xgal is added to the cell medium. Any cell with integrated HIV-1 will turn blue. Thus, this assay provides a convenient way to determine the effect of HIV inhibitors at any early step up through the expression of tat, including the inhibition of integration.

The magic cells are plated in twelve-well plates one day prior to infection. The standard assay involves infection with approximately 200 infectious units of HIV-1. This gives an approximately 20 to 1 ratio of signal to background and sufficient numbers of infectious events to quantitate dim effects. The cells are pretreated with drug for 4 hours prior to virus infection, and virus adsorption takes place for 1 hour. The cells are washed with plain medium, and then medium with inhibitor is placed back on the cells. Two days later the cells are fixed after integration with Xgal the indicator reagent for $\beta$-galactosidase production. The number of $\beta$-galactosidase expressing cells are quantitated by light microscopy.

The results of comparisons of infectious units with or without various concentrations of the bis-benzimididazoles drugs in the magic cell assay are expressed as IC$_{50}$ values and are compiled in Table 2 above. Note that the best anti-HIV compounds were generally also the best integrase inhibitors.

The foregoing is illustrative of the present invention and is not to be construed as limiting thereof. The invention is defined by the following claims, with equivalents of the claims to be included therein.

That which is claimed is:

1. A method for treating an HIV infection in a subject having an HIV infection, said method comprising administering a compound of Formula I:

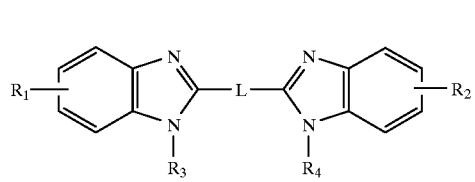

(I)

wherein:

L is a linking group selected from the group consisting of:

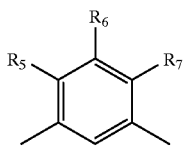

,

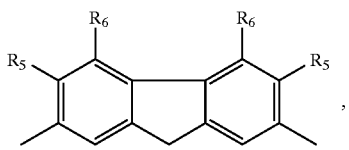

,

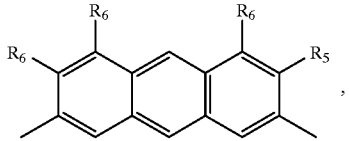

,

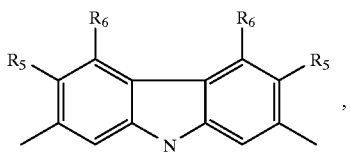

,

-continued

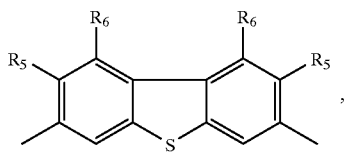

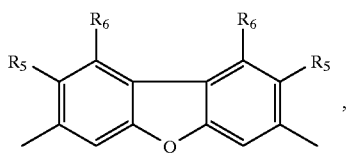

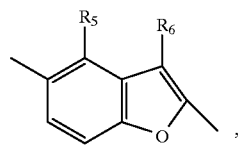

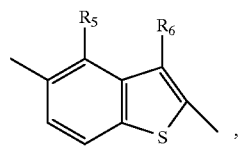

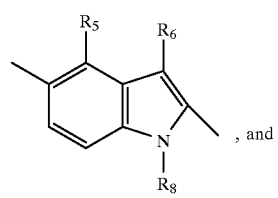

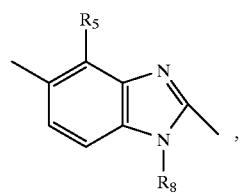

wherein $R_5$, $R_6$, $R_7$, and $R_8$ are each individually selected from the group consisting of H, alkyl, halo, aryl, arylalkyl, aminoalkyl, aminoaryl, oxoalkyl, oxoaryl, and oxoarylalkyl;

$R_1$ and $R_2$ are each individually selected from the group consisting of

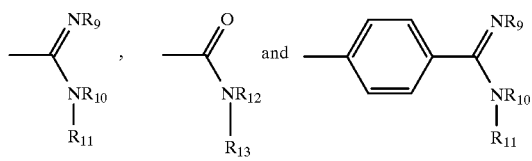

wherein $R_9$ and $R_{10}$ are each individually selected from the group consisting of H, hydroxyl, and alkyl, or $R_9$ and $R_{10}$ together represent a group selected from the group consisting of —$(CH2)_n$— where n is 2, 3, or 4, and

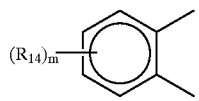

where m is 1, 2, or 3; and $R_{14}$ is H or —$CONHR_{15}R_{16}R_{17}$, wherein $R_{15}$ is lower alkyl and $R_{16}$ and $R_{17}$ are each independently selected from the group consisting of H and lower alkyl;

$R_{11}$ is H or alkyl;

$R_{12}$ is H or alkyl;

$R_{13}$ is selected from the groups consisting of alkyl, alkylamine, alkylmorpholino, and alkylaminophenyl; and $R_3$ and $R_4$ are each individually selected from the group consisting of H, alkyl and alkoxy; and pharmaceutically acceptable salts thereof; in an amount effective to treat said HIV infection.

2. A method according to claim 1, wherein L is

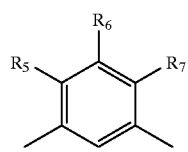

3. A method according to claim 1, wherein L is

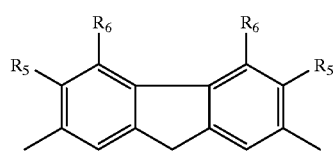

4. A method according to claim 1, wherein L is

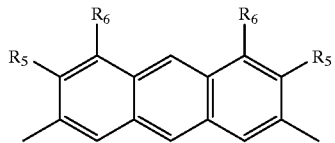

5. A method according to claim 1, wherein L is

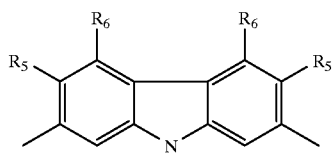

6. A method according to claim 1, wherein L is

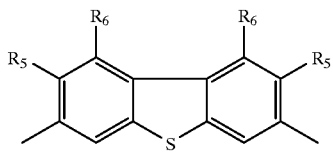

7. A method according to claim 1, wherein L is

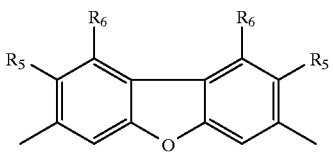

8. A method according to claim 1, wherein L is

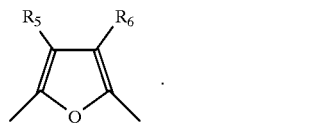

9. A method according to claim 1, wherein L is

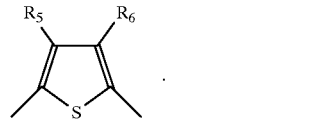

10. A method according to claim 1, wherein L is

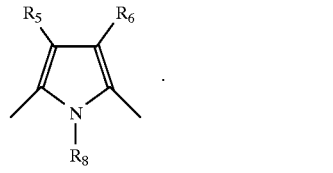

11. A method according to claim 1, wherein L is

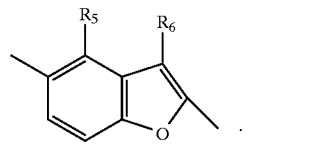

12. A method according to claim 1, wherein L is

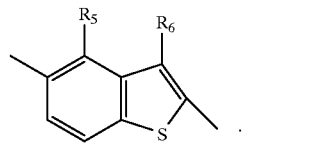

13. A method according to claim 1, wherein L is

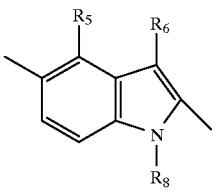

14. A method according to claim 1, wherein L is

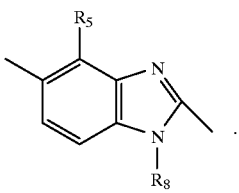

15. A method according to claim 1, wherein $R_1$ and $R_2$ each are

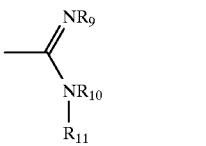

wherein $R_9$, $R_{10}$, and $R_{11}$ are each H.

16. A method according to claim 1, wherein $R_1$ and $R_2$ each are

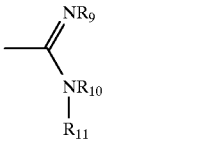

wherein $R_{10}$ is alkyl and $R_9$ and $R_{11}$ are each H.

17. A method according to claim 1, wherein $R_1$ and $R_2$ each are

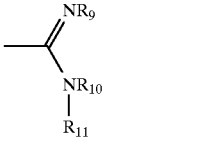

wherein $R_9$ and $R_{10}$ together are $-(CH_2)_n-$ where n is 2, 3, or 4, and $R_{11}$ is H.

18. A method according to claim 1, wherein $R_1$ and $R_2$ each are

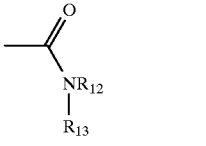

wherein $R_{12}$ is H and $R_{13}$ is alkyl.

19. A method according to claim 1, wherein $R_1$ and $R_2$ each are

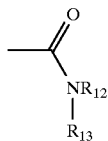

wherein $R_{12}$ is H and $R_{13}$ is alkylamino.

20. A method according to claim 1, wherein $R_1$ and $R_2$ each are

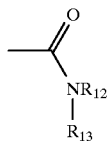

wherein $R_{12}$ is H and $R_{13}$ is alkylmorpholino.

21. A method according to claim 1, wherein $R_1$ and $R_2$ each are

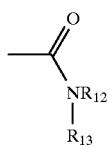

wherein $R_{12}$ is H and $R_{13}$ is alkylaminophenyl.

22. A method according to claim 1, wherein $R_1$ and $R_2$ each are

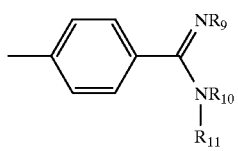

wherein $R_9$, $R_{10}$, and $R_{11}$ each H.

23. A method according to claim 1, wherein $R_1$ and $R_2$ each are

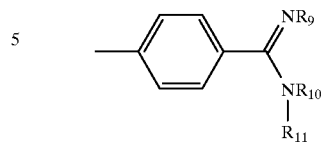

wherein $R_9$, and $R_{11}$ are each H, and $R_{10}$ is alkyl.

24. A method according to claim 1, wherein $R_1$ and $R_2$ each are

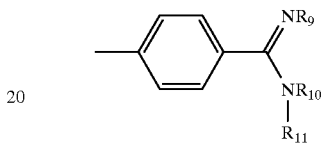

wherein $R_9$ and $R_{10}$ together are —$(CH_2)_n$— where n is 2, 3, or 4, and $R_{11}$ is H.

25. A method according to claim 1, wherein said compound is selected from the group consisting of 2,5-bis(5-amidino-2-benzimidazolyl)pyrrole;

2,5-bis-[5-(2-imidazolinyl)-2-benzimidazolyl]pyrrole;
1-methyl-2,5-bis(5-amidino-2-benzimidazolyl)pyrrole;
1-methyl-2,5-bis[5-(2-imidazolyl)-2-benzimidazolyl]pyrrole;
1-methyl-2,5-bis[5-(1,4,5,6-tetrahydro-2-pyrimidinyl)-2-benzimidazolyl]pyrrole;
2,5-bis(5-amidino-2-benzimidazolyl)furan;
2,5-bis[5-(2-imidazolinyl)-2-benzimidazolyl]furan;
2,5-bis(5-N-isopropylamidino-2-benzimidazolyl)furan;

and physiologically acceptable salts thereof.

* * * * *